US005541282A

United States Patent [19]

Walters et al.

[11] Patent Number: 5,541,282
[45] Date of Patent: Jul. 30, 1996

[54] AROMATIC POLYHYDROXY COMPOUNDS AND PROCESS FOR THE PREPARATION THEREOF

[75] Inventors: Marlin E. Walters, West Columbia; W. Frank Richey; Emmett L. Tasset, both of Lake Jackson, all of Tex.

[73] Assignee: The Dow Chemical Company, Midland, Mich.

[21] Appl. No.: 336,597

[22] Filed: Nov. 9, 1994

Related U.S. Application Data

[62] Division of Ser. No. 922,450, Jul. 30, 1992, Pat. No. 5,382,710, which is a division of Ser. No. 626,597, Dec. 12, 1990, Pat. No. 5,136,110, which is a continuation-in-part of Ser. No. 472,508, Jan. 29, 1990, abandoned.

[51] Int. Cl.$^6$ ............... C08G 59/00; C08G 65/08
[52] U.S. Cl. ............... 528/98; 528/171; 528/176; 528/196; 568/718; 568/720; 568/722; 568/723
[58] Field of Search ............... 568/718, 722, 568/723, 720; 528/98, 176, 196, 171

[56] References Cited

U.S. PATENT DOCUMENTS

| | | | |
|---|---|---|---|
| 2,634,297 | 4/1953 | Moyle | 568/718 |
| 2,858,342 | 10/1958 | Bender et al. | 568/718 |
| 3,001,972 | 9/1962 | Christenson et al. | 568/718 |
| 3,378,518 | 4/1968 | Doyle | 568/718 |
| 3,624,131 | 11/1971 | Beckes | 568/718 |
| 4,048,200 | 9/1977 | Tresper et al. | |
| 4,201,878 | 5/1980 | Mark et al. | |
| 4,467,122 | 8/1984 | Szabolcs | 568/718 |
| 5,382,710 | 1/1995 | Walters et al. | |

FOREIGN PATENT DOCUMENTS

| | | |
|---|---|---|
| 1092027 | 3/1958 | Germany. |
| 2919757 | 11/1980 | Germany. |
| 1296024 | 12/1986 | Japan. |
| 259746 | 3/1988 | Japan. |
| 885005 | 12/1961 | United Kingdom. |
| 894620 | 4/1962 | United Kingdom. |
| 935061 | 8/1963 | United Kingdom. |

OTHER PUBLICATIONS

Morgan, vol. 3 #5 Macromolecules 536 Sep. 1970.
*Justus Liebig's Annalen der chemie* 363: pp. 275–276 Jul. 1908.
Chemical Abstract 29:855 Jul. 1935.
Chemical Abstract 65:3795c Aug. 1966.
J. Amer. Chem. Soc. 37, pp. 2575–2591 Sep. 1915.
Chemical Abstract 85:192405k (Japan Kokai 76 86,434) Jul. 1976.
J. Amer. Chem. Soc. 61, pp. 345–348 Feb. 1939.
J. Amer. Chem. Soc. 76, pp. 4547–4550 Sep. 1954.

*Primary Examiner*—James J. Seidleck
*Assistant Examiner*—John M. Cooney, Jr.

[57] ABSTRACT

The invention involves aromatic polyhydroxy compounds, including triaromatic bisphenols and tris-[1,1,1-(4-hydroxyphenyl)] toluenes, and a process for the preparation thereof by reacting a phenolic compound, e.g. phenol, with a suitable halo-compound, for instance 1,1-dichloroethylbenzene, 1-chlorostyrene, or mixtures thereof. The reaction may be conducted in the presence or absence of a solvent; an excess of the phenolic compound can serve as the solvent. The product is conveniently recovered by removing the by-product HCl, excess phenolic compound, excess solvent and cooling. Yields of bis-1,1-(4-hydroxyphenyl)-1-phenylethane which are greater than 90% of theoretical have been obtained by the reaction of phenol and 1,1-dichloroethylbenzene, and a large portion of the yield is para isomer. Suitable halo-compounds include aromatic dihalo-compounds having at least one aliphatic substituent having two alpha-halogen atoms and at least one beta halogen atom, halo-styrenes having structures corresponding to such aromatic dihalo-compounds except that an alpha-halogen atom and a beta hydrogen atom are removed and there is a double bond between the alpha and beta carbon atoms, trihalotoluenes, and dihalocyanotoluenes.

20 Claims, No Drawings

AROMATIC POLYHYDROXY COMPOUNDS AND PROCESS FOR THE PREPARATION THEREOF

CROSS REFERENCE TO RELATED APPLICATIONS

This is a division of application Ser. No. 07/922,450 filed Jul. 30, 1992 now U.S. Pat. No. 5,382,710 which is a division of application Ser. No. 07/626,597, filed Dec. 12, 1990, now U.S. Pat. No. 5,136,110, which is a continuation-in-part of application Ser. No. 07/472,508, filed Jan. 29, 1990, now abandoned.

BACKGROUND OF THE INVENTION

This invention relates to aromatic polyhydroxy compounds and the preparation thereof, particularly bisphenols having a carbon atom having bonded thereto an aliphatic group and at least three aromatic groups, at least two of which aromatic groups each have at least one phenolic group, hereinafter referred to as triaromatic bisphenols. Bisphenols and other aromatic polyhydroxy compounds are the building block molecules for such materials as polycarbonates, epoxy resins, polysulfones, polyarylates and the like. Bisphenols in which the phenolic rings are joined together through a single bridging carbon are usually manufactured by condensing two moles of phenol with an aldehyde or a ketone in the presence of an acid catalyst. Bisphenol-A is the most commonly used bisphenol and is made from the reaction of acetone with phenol. Because it must be performed under mild temperature conditions (50°–70° C.) to minimize the formation of undesirable coproducts, it is a slow reaction. Other bisphenols are employed to impart specific properties to the above resins. Some of these properties are, for example, toughness, strength, better thermal properties and solvent resistance. Bisphenol-AP, the bisphenol of phenol and acetophenone (bis-1, 1-(4-hydroxyphenyl)-1-phenylethane), is known to improve the thermal properties of polycarbonates, polyarylates and epoxy resins over similar materials made from Bisphenol-A.

The condensation of phenol with acetophenone, however, is very slow. Even with zinc chloride as a catalyst, the reaction requires two days to complete (U.S. Pat. No. 4,467,122). Then an extended work-up must be performed to remove as much residual zinc salt as possible. With HCl as the catalyst, the reaction requires 1–14 days. These process limitations, along with the lack of commercially significant quantities of acetophenone, have hindered the development of useful applications for Bisphenol-AP. A more facile process should allow wider use of this valuable monomer.

In order to achieve the high molecular weights required to produce the desired thermal and mechanical properties, the bisphenol starting materials for such thermoplastics as polycarbonates and polyarylates preferably have the constituent phenol groups substituted in the para position in greater than 98 percent selectivity. Although most of the ortho-substituted material can be separated by crystallization, it is most desirable for good process economics to minimize the product containing any ortho isomer. In one reference, [*J. American Chemical Society*, 76, 4547 (1954)], 1-chloroethylbenzene is reported to react with phenol to give a mixture of isomers of 1-(hydroxyphenyl)-1-phenylethane having the hydroxy group of the phenyl group in the ortho and para position in a mole ratio of 55 ortho to 45 para position.

It would be desirable to prepare triaromatic bisphenols more quickly than is typical for condensations of acetophenone with phenols and to prepare them such that there is a high selectivity for the para isomer. Bishydroxyphenyl compounds, including triaromatic bisphenols, are preferably in the para isomer form (having the hydroxy group on the phenyl ring para to the attachment of the phenyl ring to the carbon atom to which the other phenyl group(s) are attached) because such isomers result in high polymers with desirable properties of high molecular weight, impact strength, modulus and the like.

SUMMARY OF THE INVENTION

Bisphenols and other aromatic polyhydroxy compounds are made by reacting a halo-compound which is (1) a trihalotoluene, (2) a dihalocyanotoluene, (3) an aromatic dihalo-compound having at least one aliphatic substituent having two alpha-halogen substituents and at least one beta hydrogen atom, (4) a corresponding halo-styrene or (5) mixtures thereof with a phenolic compound. At least two moles of the phenolic compound per mole of halo-compound are preferably employed. The reaction may be conducted with or without a solvent. The bisphenol is conveniently recovered by removing by-product HCl (or other halide compound), excess phenolic compound and solvent (if any) and cooling to obtain the product. Alternatively, a crystallization solvent is used.

In contrast with conventional technology, the new method is rapid and uses a simple purification to give the desired product. For instance, yields of bis-1,1-(4-hydroxyphenyl)-1-phenylethane (Bisphenol-AP) of up to 95 percent of theoretical can be obtained using this process.

The reaction is broadly applicable with other aromatic hydroxy compounds such as naphthols and substituted phenols which can be reacted with the halo-compounds in place of phenol to prepare analogous bis hydroxyaromatic derivatives.

There is advantageously high selectivity for the para isomers. For instance, we have now discovered that under mild conditions, the reaction of phenol with 1,1-dichloroethylbenzene (DCEB) will produce Bisphenol-AP rapidly with excellent selectivity to the p,p' isomer, preferably with greater than 94% selectivity. This selectivity is unexpected in view of the known art.

The invention also involves aromatic polyhydroxy compounds which are tris-[1,1,1-(4-hydroxyphenyl)] toluenes, and polymers prepared therefrom.

DETAILED DESCRIPTION OF THE INVENTION

The process of the invention is represented by the reaction:

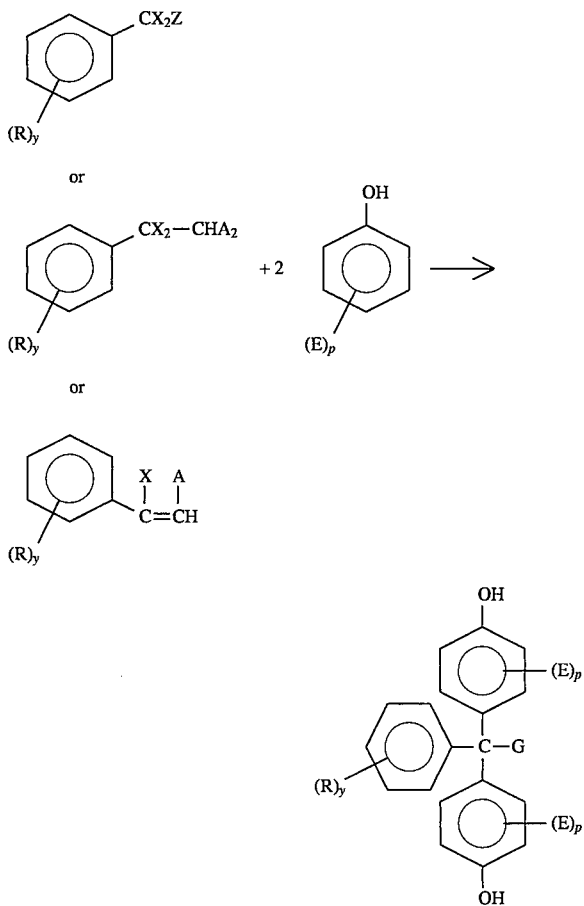

wherein each A is independently H or an aliphatic group; each R or E is independently an inert substituent or an aliphatic or aromatic group wherein two or more R's and/or 2 or more E's are optionally joined to form cycloaliphatic or aromatic groups; G is CN or (E)p-phenyl-OH in the case of the —$CX_2Z$ starting material, —$CHA_2$ in the case of the dihalo starting material or —$CH_2A$ in the case of the halostyrene starting material; X is a halogen, either chlorine or bromine, preferably chlorine; Z is a chlorine, bromine or a cyano group (CN); y is an integer of from 0 to 5, preferably from 0 to about 2, more preferably from 0 to 1; and p is an integer of from 0 to 4, preferably from 0 to about 2, most preferably from 0 to 1. When A is an aliphatic group, each A preferably has from 1 to about 15 carbon atoms, more preferably from 1 to about 5 carbon atoms. Each aliphatic R, A or E is unsubstituted or optionally inertly substituted. By inert substituent or inertly substituted, it is meant that the substituent is one which does not undesirably interfere with the reaction of the aromatic halo-compound with a phenolic compound.

Compounds wherein G is (E)p-phenyl-OH are referred to herein as tris-[1,1,1-(4-hydroxyphenyl)] toluenes and are new compounds useful in making polymers. In an embodiment which is an alternative to the reaction scheme diagramed above, tris-[1,1,1-(4-hydroxyphenyl)] toluenes may be prepared with at least 3 moles of phenolic compound. The term "aromatic polyhydroxy compound" may be used to refer to either a triaromatic bisphenol or a tris-[1,1,1-(4-hydroxyphenyl)] toluene, as described above.

In the illustrated reaction sequence, the compounds having X substituents are those referred to herein as halo-compounds. The halo-compounds include dihalo alkyl aromatic compounds having an aliphatic substituent, said substituent having two alpha-halogen atoms (attached to an alpha carbon atom which is attached to an aromatic ring) and at least one beta hydrogen atom (attached to a beta carbon atom which is attached to the alpha carbon atom having the halogen atoms), optionally inertly substituted trihalotoluenes and cyanodihalotoluenes, and halo-styrene compounds corresponding to the dihalo alkyl aromatic compounds in structure except that one halogen atom and the beta hydrogen atom are eliminated and a double bond is present between the alpha and beta carbon atoms. Either type of halo-compound is suitable for use in the practice of the invention. Suitable halo-compounds include 1-chlorostyrene; 1,1-dichloroethylbenzene (DCEB); 1-bromostyrene; 1,1-dibromoethylbenzene; 1,1-dichloro-n-hexylbenzene; 1,1,1-trichlorotoluene; 1,1,1-tribromotoluene; o-methyl-1,1,1-trichlorotoluene; 1-cyano-1,1-dichlorotoluene; m-ethyl-1,1,1-trichlorotoluene and the like and mixtures thereof. Preferred compounds are 1-chlorostyrene, 1,1-diehloroethylbenzene and mixtures thereof. Such compounds wherein all the halogen atoms are chlorine are referred to herein as chloro-compounds.

The process of the present invention can be illustrated by the process for making bis-1,1-(4-hydroxyphenyl)-1-phenylethane (Bisphenol-AP) by contacting (a) 1,1-dichloroethylbenzene or 1-chloro-styrene or a mixture thereof, with (b) phenol, wherein the phenol is preferably present in an amount equivalent to at least a two molar multiple of the amount of (a) present. Reactants are preferably in liquid form. For instance, the halo-compound can be employed as a neat liquid and the phenol can be in its molten form or either one or both reactants can be dissolved in an inert solvent prior to contacting. After the reaction is desirably complete, the product bisphenol is recovered. For instance, the reaction mixture can be cooled to effect crystallization of the product bisphenol.

Any method of recovery within the skill in the art is suitable. An alternative method of recovering the product is to remove the unreacted phenolic compound, the HCl produced in the reaction and solvent (if any) prior to cooling to effect the crystallization of the bisphenol. Yet another way of recovering the product is to remove most of the unreacted phenolic compound, then to add a solvent and cool to effect the crystallization of the bisphenol.

Although the reaction is autocatalytic because the HCl produced by the reaction is an effective catalyst, any strong acid catalyst, advantageously HCl or any other hydrogen halide, may be added to the phenol as a catalyst for the reaction, preferably before the addition of the halo-compound because addition of the acid catalyst is more useful before the concentration of HCl produced in the reaction has reached a desired catalytic concentration. It is advantageous to conduct the reaction under a pressure greater than atmospheric by the use of a hydrogen halide, e.g. hydrogen chloride. The pressure of the hydrogen halide may vary from about 1 to about 100 atmospheres, preferably from about 1 to about 10 atmospheres.

Triaromatic bisphenols (analogous to Bisphenol-AP), can be prepared from aromatic hydroxyl compounds (any phenolic or thiophenolic compound which reacts with the halo-compound) such as naphthols, hydroxybiphenyl substituted phenols and the like by reacting them with the halo-compounds. Thus, for example, naphthols, hydroxybiphenyls, alkylphenols, dialkylphenols thiophenols, nitrophenols and halophenols can be employed in place of the phenol reactant in the process. Specific hydroxyaromatic compounds useful in the reaction include o- and m-cresols, 2,6-dimethyl-phenol, nonylphenol, o- and m-chlorophenols, 2-naphthol, 1-naphthol, ethylphenol, 2-methylthiophenol, resorcinol, 2-nitrophenol, 3-nitrophenol, 2-chloro-thiophenol and the like. Preferred compounds include alkyl phenolic having alkyl groups of from 0 to about 5 carbon atoms and phenol; more preferred is phenol.

Any molar ratio of phenolic compound to halo-compound which results in formation of the bisphenol is suitable but at least a stoichiometric molar ratio of at least two moles of phenolic compound to halo-compound is preferred, more preferably an excess of the stoichiometric amount of phenolic compound is used. Preferred mole ratios of phenolic compound to halo-compound are from about 2:1 to about 40:1 with about 5:1 to about 25:1 more preferred and from about 5:1 to 15: most preferred. These molar ratios are preferred because they result in greater yields of bisphenol products and decrease yields of polymeric products formed by reaction of a halo-compound with the reaction product of one mole of chloro-compound with one mole of phenolic compound. Use of a large excess of phenolic compound e.g. greater than about 25:1 is generally less preferred because it is wasteful of phenolic compounds or requires voluminous recycle.

The reaction temperature is preferably from about −20° C. to about +100° C., more preferably from about 20° to about 50° C., and most preferably about room temperature. Temperatures above the preferred range can promote undesirable reactions, while those below the range make it difficult to maintain the reaction mass in molten condition (if no solvent is used) or will unduly slow the rate of reaction. Lower temperatures are, however, suitable when a solvent is used, but slower reaction rates are generally observed.

Reaction solvents may include any solvent for the reactants which does not react undesirably with either the reactants or the products under reaction conditions. Preferred solvents include chlorinated aliphatic compounds, e.g. chloroform, carbon tetrachloride, trichloroethylene and the like; aromatic hydrocarbons, e.g. benzene, ethylbenzene and toluene; aromatic ethers such as phenyl ether; and halogenated aromatics such as chlorobenzene. Excess phenolic compound can also serve as a solvent for the reaction. Other useful solvents include tetrahydrofuran, acetic acid and nitriles such as acetonitrile.

Trihalotoluenes and dihalocyanotoluenes are commercially available and can be prepared by means within the skill in the art. The aromatic dihalo-compounds having at least two alpha halogen atoms and at least one beta hydrogen atom, for instance 1,1-dichloroethylbenzene can be made by the chlorination of corresponding halohydrocarbons, for instance 1-chloroethylbenzene, with molecular halogen using a phosphorus halide catalyst, e.g. $PCl_3$ or $PCl_5$, in the presence of light or other initiator (see British Pat. No. 1,563,164).

A new and better method of making dihalo-compounds such as 1,1-dichloroethylbenzene is taught in a co-filed application of two of the present inventors in which either organic or inorganic hypochlorites are reacted with ethylbenzene to obtain good selectivity to 1,1-dichloroethylbenzene. The application referred to is "Method for the Selective Alpha Halogenation of Alkylaromatic Compounds", U.S. application Ser. No. 472,507 filed Jan. 29, 1990. That application is incorporated herein by reference with respect to the teachings concerning the method of making the dihalo reactant of the present application. A reactive hypohalite compound is reacted with an alkyl aromatic compound having at least one aliphatic substituent and which contains at least two alpha-hydrogens and in which each aliphatic substituent has at least one beta-hydrogen in the presence of a free radical generating medium. Useful hypohalites include alkali metal hypohalites used with phase transfer catalyst and t-alkyl hypohalites such as t-butyl hypochlorite. At least 2 moles of hypohalite are used for each mole of alkylaromatic compound. Useful free radical catalysts include peroxides such as t-butyl peroxide and t-amyl peroxide and hydroperoxides such as chloro-t-butyl hydroperoxide, cumene hydroperoxide and cyclohexane hydroperoxide. Diazo compounds and diacyl peroxides are similarly useful. Representative alkyl aromatic compounds include ethylbenzene, n-propylbenzene, n-butylbenzene, n-octylbenzene, n-decylbenzene, n-dodecylbenzene, ethylphenyl acetate, ethylnaphthalene, diethylbenzene, diethylbiphenyl, n-propylbiphenyl, ethylthiophene and the like.

Dehydrochlorination of 1,1-dichloroethylbenzene or other such dihalo-compounds having a beta hydrogen will produce the corresponding 1-halostyrene which is employed in the process of the present invention for the preparation of the triaromatic bisphenols.

The halo-compound, for instance 1,1-dichloroethylbenzene or 1-chlorostyrene, is added to the molten phenolic compound or, optionally, to the phenolic compound in solution, and reacted at a suitable temperature. The phenolic compound is preferably employed in excess to limit the formation of higher molecular weight phenolics. To form a bisphenol in good yield, the phenolation (reaction of phenolic compound with halo-compound) requires at least two moles of phenolic compound for each mole of the halo-compound.

When the reaction is conducted by reacting a 1-halostyrene, trihalotoluene or dihalocyanotoluene with the phenolic compound, the conditions are substantially the same as when using the dihalo-compounds illustrated by 1,1-dichloroethylbenzene. When mixtures of suitable dihalo-compounds, trihalotoluenes, cyanodihalotoluenes and/or 1-halostyrenes are employed, the mole ratios and other conditions and parameters are substantially the same as when using either of these reactants separately.

It is advantageous to avoid water in the reaction between the phenolic compound and the halo-compound because, in the presence of acid, the halo-compounds react with water to form acetophenone. Acetophenone, thus, may be present even though it is not a reactant in the process of the invention. To avoid this side-reaction it is preferred to dry the reactants or use anhydrous reagents, catalysts and solvents for the reaction. It is also advantageous to maintain an atmosphere inert to the reaction mixture or to catalytic acid such as hydrogen chloride rather than to allow air (with its moisture) to contact the reaction mixture.

The reaction is preferably allowed to proceed to a preselected degree of completion before recovery of product. Any degree of completion is suitable, but yield is improved by allowing the reaction to produce as much product as the reaction will produce under reaction conditions within a convenient length of time. More preferably, a degree of completion corresponding to a yield of at least about 80 percent is preselected. Most preferably, the preselected degree of completion is that corresponding to substantial disappearance of halo-compound, that is disappearance of at least about 90 weight percent of the halo-compound, more preferably of all halo-compound detectable by laboratory means such as gas chromatography.

Methods of recovering product bisphenols from reaction mixtures are within the skill in the art. Conveniently, when there is little excess phenolic compound remaining in the reaction mixture, a crystallization solvent is added to the reaction mixture to precipiate product. Advantageously, when excess phenolic compound is present, it is removed by means within the skill in the art before a crystallization solvent is added to precipitate the product. Convenient crystallization solvents include aromatic hydrocarbons such as toluene, ethylbenzene and chlorobenzene; chlorinated aliphatics such as chloroform and carbon tetrachloride; ketones such as acetone and methyl ethyl ketone; and esters such as diethyl carbonate and mixtures of these solvents. Crystallization is advantageously enhanced by cooling of the reaction mixture before or after addition of the crystallization solvent. Cooling alone is sometimes sufficient to cause precipitation of product without addition of crystallization solvent. Before crystallization, hydrogen chloride is optionally, but preferably, removed by means within the skill in the art such as distillation.

The process of the invention advantageously produces triaromatic bisphenols having a high percentage of para isomer (the hydroxyl group on a phenyl ring is para to the ring position of attachment of the carbon atom to which the three aromatic groups are attached). The mole ratio of para to ortho isomers is advantageously equal to or greater than at least about 60:40, preferably at least about 75:25, more preferably at least about 90:10, most preferably at least about 95:5. While the process of the invention generally produces products having these high ratios of para to ortho isomers, other methods of preparing the triaromatic bisphenols generally produce products having lower ratios of para to ortho isomers than those ratios produced in the practice of the invention.

The following experiments are representative of the invention:

EXAMPLE 1.

Preparation of Bisphenol-AP by reacting DCEB and phenol.

Anhydrous phenol (3791.2 g, 40.28 mols) is transferred from a nitrogen-padded drum held at 78° C. to a 5-L three-neck flask equipped with thermocouple, magnetic stirring bar, a nitrogen inlet and a 600 mL dropping funnel (vented through a scrubber to neutralize the HCl acid off-gas). A nitrogen atmosphere is maintained throughout the reaction by a continuous flow of nitrogen gas through the nitrogen inlet. The temperature is maintained with a heating mantle. The phenol is allowed to cool to 50° C. and maintained at that temperature with a heating mantle. 1,1-Dichloroethylbenzene (DCEB) (700.2 g, 4.0 mols) is charged to the dropping funnel and addition is begun at a rate that will complete it in about 4 hours. The phenol solution turns bright red immediately upon addition of DCEB and evolution of HCl (hydrochloric acid) begins within a few minutes. The reaction mixture is stirred continually and held at the 50° C. temperature for one hour after the addition is complete. A sample is analyzed by gas chromatography (G.C.) at this time to determine the completeness of the reaction. When completion of the reaction is indicated by disappearance of the peak corresponding to the halo-compound (DCEB), a distillation head is placed on the flask and the bulk of the phenol removed at aspirator pressure (ca. 50 mm Hg). The reaction flask is then allowed to cool to room temperature and 2L of $CCl_4$ (carbon tetrachloride) is added with stirring. When this solution is cooled to room temperature and filtered, 904.8 g (78% of theoretical yield) of white crystals (m.p. 187°–89° C.) are obtained. The crystallized product is bis-1,1-(4'-hydroxyphenyl)-1-phenylethane (4,4'-Bisphenol AP) and contains no detectable bis-1-1-(2,4'-hydroxyphenyl)-1-phenylethane (2,4'-Bisphenol AP).

EXAMPLES 2–15.

Preparation of Bisphenol-AP employing different parameters.

Other experiments are conducted in the manner of Example 1 employing different temperatures, ratios of phenol to 1,1-dichloroethylbenzene, and other solvents. In some examples, additional HCl is supplied to the reaction mixture by sparging the mixture with HCl to the point of saturation. Conditions of the reactions and the results are shown in Table I.

TABLE I

| Ex. No. | Ratio of DCEB/Solvent (weight percent) | Ratio of Phenol/Solvent (weight percent) | Mol Ratio Phenol/DCEB | HCl (saturated) | Temp. (°C.) | Mole percent Yield | Mole percent bis-1,1-(4-hydroxyphenyl)-1-phenylethane |
|---|---|---|---|---|---|---|---|
| 2 | /none | /none | 3.6 | no | 43 | 37 | 97.1 |
| 3 | /none | /none | 12.8 | yes | 43 | 80 | 94.6 |
| 4 | /none | /none | 11.6 | no | 43 | 81 | 95.7 |
| 5 | /none | /none | 16.2 | yes | 43 | 77 | 96.8 |
| 6 | /none | /none | 17.7 | no | 43 | 79 | 95.6 |
| 7 | /none | /none | 17.9 | yes | 42–34 | 84 | 97.4 |
| 8 | /none | /THF (79%) | 19.6 | yes | 40 | 57 | 99.0 |
| 9 | /none | /$CCl_4$ (89%) | 11.2 | no | 35 | 71 | 98.2 |
| 10 | /$CCl_4$ (29%) | /none | 18.1 | yes | 40 | 85 | 96.8 |
| 11 | /none | /$CCl_4$ (24%) | 6.4 | no | 27 | 58 | 100 |
| 12 | /none | /$CCl_4$ (66%) | 11.5 | no | 25 | 75 | 97.8 |
| 13 | /$CCl_4$ (18%) | /$CCl_4$ (66%) | 22.6 | yes | 25 | 87 | 97.9 |
| 14 | /$CCl_4$ (18%) | /$CCl_4$ (66%) | 22.6 | yes | 25 | 89 | 98.1 |
| 15 | /$CCl_4$ (18%) | /$CCl_4$ (66%) | 22.6 | yes | 25 | 89 | 98.1 |

EXAMPLES 16 and 17

Preparation of Bisphenol-AP by reacting α-chlorostyrene with phenol.

In the manner of Example 1, α-chlorostyrene (α-CS) is substituted for DCEB in the reaction with phenol to make the Bisphenol-AP. Conditions and results are shown in Table II.

TABLE II

| Ex. No. | Ratio of α-CS/ solvent (weight percent) | Ratio of Phenol/ solvent (weight percent) | Mol Ratio: Phenol/ α-CS | HCl (saturated) | Temp. (°C.) | % Yield | Mole Percent bis-1,1-(4-hydroxy phenyl)-1phenyl ethane |
|---|---|---|---|---|---|---|---|
| 16 | /none | /none | 51.5 | yes | 43 | 83 | 95.7 |
| 17 | /none | /CCl$_4$ (64%) | 10.2 | yes | 25 | 76 | 97.8 |

EXAMPLE 18.

Preparation of Bisphenol-AP by reacting DCEB and phenol.

In yet another preparation, anhydrous molten phenol (4350.6 g, 46.22 moles) and 900 mL CCl$_4$ are placed in a 5-L flask fitted in the manner of Example 1. The mixture is allowed to cool to 30° C. while being sparged with HCl, and DCEB (712.46 g, 4.07 moles) is added dropwise to the stirring mixture over a 5-hour period. The mixture is allowed to stir an additional 45 min. or until G.C. analysis shows the reaction to be complete. Excess phenol is removed by distillation and 2500 mL of chlorobenzene is added with stirring and the mixture is allowed to cool to room temperature. Crystals of product are filtered, and washed with CCl$_4$. After drying in a vacuum oven at 120° C. overnight a 92% yield of Bisphenol-AP (1105.48 g) is obtained based on the starting DCEB. The product is 99.6% 4,4'-bisphenol AP. The crystallized product contains no detectable 2,4'-bisphenol AP.

EXAMPLE 19

Preparation of Bisphenol-AP by reacting α-chlorostyrene and phenol in ethylbenzene solvent.

To a quantity (957.5 g) of phenol at 40° C. is added 115 g of ethylbenzene. Anhydrous HCl is bubbled through the mixture for one hour and used to bring the pressure to 10 psig (68.95 K Pa gauge). The solution is agitated while 201.3 g of α-chlorostyrene in 300 g ethylbenzene is continuously fed into the reaction mixture (one-half over a 5-hour period and the remainder in an additional 7 hour period). The temperature of the reaction mixture is lowered gradually to 32° C. over the first 80 minutes and maintained there for the remainder of the 12-hour reaction period. Analysis of the reaction mixture by liquid chromatography shows a selectivity to Bisphenol-AP of 917 (98.9% 4,4'-bisphenol AP) based on a-chlorostyrene. The actual yield of product recovered by crystallization is 89% (100% 4,4'-bisphenol AP), based on the α-chlorostyrene.

EXAMPLE 20

Using 1,1,1-Trichlorotoluene to prepare Tris-[1,1,1-(4-Hydroxyphenyl)] toluene

In a manner of Example 1, benzotrichloride (0.35 moles, 69.0 g) is added to phenol (7.24 moles, 681.4 g) dissolved in carbon tetrachloride (2.59 moles, 398.5 g) over a 4 hour period. The reaction mixture turns bright red and vents HCl immediately upon the addition of the First drops of benzotrichloride. The excess phenol is distilled at aspirator vacuum, and the product is crystallized from diethylcarbonate. Analysis of proton nuclear magnetic resonance (HNMR) shows peaks from a tetramethylsilane standard of δ6.8 (q,12H), δ7.1(s,5H), δ8.5(s,3H) (q=quartet, s=singlet) corresponding to a structure of tris-[1,1,1-(4-hydroxyphenyl)] toluene. The melting point is measured as 272°–275° C.

We claim:

1. A polymer prepared from a tris-[1,1,1-(4-hydroxyphenyl)] toluene described by formula as follows:

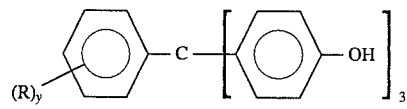

wherein R is independently an inert substituent or an aliphatic or aromatic group, two or more R's are optionally joined to form cycloaliphatic or aromatic groups, and y is an integer of from 0 to 5; which has a mole ratio of isomers in which the hydroxy aromatic rings are bonded at the para position to those isomers in which the hydroxy aromatic rings are bonded at the ortho position of at least about 60:40.

2. The polymer of claim 1 wherein, in the tris-[1,1,1-(4-hydroxyphenyl)] toluene used in preparation thereof, R is an aliphatic group.

3. The polymer of claim 1 wherein, in the tris-[1,1,1-(4-hydroxyphenyl)] toluene used in preparation thereof, R is an aromatic group.

4. The polymer of claim 1 wherein, in the tris-[1,1,1-(4-hydroxyphenyl)] toluene used in preparation thereof, R is an inert substituent.

5. The polymer of claim 1 wherein, in the tris-[1,1,1-(4-hydroxyphenyl)] toluene used in preparation thereof, R is hydrogen.

6. The polymer of claim 1 wherein, in the tris-[1,1,1-(4-hydroxyphenyl)] toluene used in preparation thereof, y is an integer of from 0 to 2.

7. The polymer of claim 1 which is a polycarbonate, an epoxy resin, a polysulfone or a polyarylate.

8. The polymer of claim 1 which is a polycarbonate.

9. The polymer of claim 1 which is an epoxy resin.

10. The polymer of claim 1 wherein the tris-[1,1,1-(4-hydroxyphenyl)] toluene used in preparation thereof has a mole ratio of para isomers to ortho isomers of at least about 75:25.

11. The polymer of claim 1 wherein the tris-[1,1,1-(4-hydroxyphenyl)] toluene used in preparation thereof has a mole ratio of para isomers to ortho isomers of at least about 90:10.

12. The polymer of claim 1 wherein the tris-[1,1,1-(4-hydroxyphenyl)] toluene used in preparation thereof has a mole ratio of para isomers to ortho isomers of at least about 95:5.

13. The polymer of claim 2 wherein the tris-[1,1,1-(4-hydroxyphenyl)] toluene used in preparation thereof has a mole ratio of para isomers to ortho isomers of at least about 75:25.

14. The polymer of claim 2 wherein the tris-[1,1,1-(4-hydroxyphenyl)] toluene used in preparation thereof has a mole ratio of para isomers to ortho isomers of at least about 90:10.

15. The polymer of claim 3 wherein the tris-[1,1,1-(4-hydroxyphenyl)] toluene used in preparation thereof has a mole ratio of para isomers to ortho isomers of at least about 75:25.

16. The polymer of claim 3 wherein the tris-[1,1,1-(4-hydroxyphenyl)] toluene used in preparation thereof has a mole ratio of para isomers to ortho isomers of at least about 90:10.

17. The polymer of claim 5 wherein the tris-[1,1,1-(4-hydroxyphenyl)] toluene used in preparation thereof has a mole ratio of para isomers to ortho isomers of at least about 75:25.

18. The polymer of claim 5 wherein the tris-[1,1,1-(4-hydroxyphenyl)] toluene used in preparation thereof has a mole ratio of para isomers to ortho isomers of at least about 90:10.

19. The polymer of claim 8 wherein, in the tris-[1,1,1-(4-hydroxyphenyl)] toluene used in preparation thereof, R is hydrogen, and the mole ratio of para isomers to ortho isomers is at least about 75:25.

20. The polymer of claim 8 wherein, in the tris-[1,1,1-(4-hydroxyphenyl)] toluene used in preparation thereof, R is hydrogen, and the mole ratio of para isomers to ortho isomers is at least about 90:10.

* * * * *